(12) United States Patent
Illsley et al.

(10) Patent No.: US 11,279,838 B2
(45) Date of Patent: *Mar. 22, 2022

(54) ELECTRON BEAM CURABLE COMPOSITIONS COMPRISING POLYOLS

(71) Applicant: SUN CHEMICAL CORPORATION, Parsippany, NJ (US)

(72) Inventors: Derek Ronald Illsley, Frome (GB); Stephen Anthony Hall, Wells (GB); Shaun Lawrence Herlihy, Glastonbury (GB)

(73) Assignee: Sun Chemical Corporation, Parsippany, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/979,242

(22) PCT Filed: Jul. 1, 2019

(86) PCT No.: PCT/GB2019/051856
§ 371 (c)(1),
(2) Date: Sep. 9, 2020

(87) PCT Pub. No.: WO2020/012157
PCT Pub. Date: Jan. 16, 2020

(65) Prior Publication Data
US 2020/0399485 A1    Dec. 24, 2020

Related U.S. Application Data

(60) Provisional application No. 62/818,772, filed on Mar. 15, 2019, provisional application No. 62/760,142, (Continued)

(51) Int. Cl.
| | | |
|---|---|---|
| *C09D 11/101* | (2014.01) | |
| *A61L 2/08* | (2006.01) | |
| *B41M 5/00* | (2006.01) | |
| *B41M 7/00* | (2006.01) | |
| *C09D 11/033* | (2014.01) | |
| *C09D 11/037* | (2014.01) | |
| *C09D 11/107* | (2014.01) | |
| *C09D 11/322* | (2014.01) | |
| *C09D 11/36* | (2014.01) | |

(Continued)

(52) U.S. Cl.
CPC ............ *C09D 11/101* (2013.01); *A61L 2/087* (2013.01); *B41J 2/2107* (2013.01); *B41M 1/04* (2013.01); *B41M 5/0047* (2013.01); *B41M 5/0064* (2013.01); *B41M 7/0081* (2013.01); *C09D 11/033* (2013.01); *C09D 11/037* (2013.01); *C09D 11/107* (2013.01); *C09D 11/322* (2013.01); *C09D 11/36* (2013.01); *A61L 2202/18* (2013.01); *A61L 2202/23* (2013.01)

(58) Field of Classification Search
CPC .... B41J 2/1433; B41J 2/1623; B41J 2202/00; B41J 2202/03; B41J 2/14201; B41J 2/045; B41J 11/0015; B41J 11/002; B41J 2/04581; B41J 2/055; B41J 2/16538; B41J 2002/16502; B41J 29/02; B41J 2/17513; B41J 2/17509; B41J 29/13; B41J 2/17553; B41J 2/1606; B41J 2/1642; B41J 2/1609; B41J 2/164; B41J 2/162; B41J 2/161; B41J 2/19; B41J 15/04; B41J 25/001; B41J 25/34; B41J 25/003; B41J 2/21; B41J 25/312; B41J 2025/008; B41J 2202/21; B41J 2/17596; B41J 2/16508; B41J 2/1652; B41J 2/175; B41J 2/17563; B41J 3/4078; B41J 11/0021; B41J 2/01; B41J 2/211; B41J 2/17; B41J 2/17593; B41J 2/2107; B41J 2/1755; B41J 2/2114; B41J 2/2117; B41J 2/2056; B41J 2/0057; B41J 3/60; B41J 2002/012; B41J 2/04598; B41F 23/042; B41F 23/0436; C09D 11/36; C09D 11/40; C09D 11/30; C09D 11/38; C09D 11/32; C09D 11/322; C09D 11/324; C09D 11/328; C09D 11/101; C09D 11/102; C09D 11/005; C09D 11/54; C09D 11/52; C09D 11/106

See application file for complete search history.

(56) References Cited

U.S. PATENT DOCUMENTS

| | | |
|---|---|---|
| 6,846,851 B2 | 1/2005 | Nakhmanovich |
| 7,208,257 B2 | 4/2007 | Cheng |

(Continued)

FOREIGN PATENT DOCUMENTS

| | | |
|---|---|---|
| WO | WO 2008/071994 A1 | 6/2008 |
| WO | WO2011/021052 A2 | 2/2011 |

(Continued)

OTHER PUBLICATIONS

International Search Report issued in International Application No. PCT/GB2019/051856, dated Sep. 2, 2019.

(Continued)

*Primary Examiner* — Manish S Shah
(74) *Attorney, Agent, or Firm* — Marian E. Fundytus; Ostrolenk Faber LLP.

(57) ABSTRACT

Electron beam curable compositions including polyols, and any blend of ethylenically unsaturated monomers and oligomers. The polyols of the invention are preferably essentially free of any ethylenically unsaturated groups, have greater than one hydroxy group and preferably have boiling points in excess of 170° C.

19 Claims, No Drawings

Related U.S. Application Data filed on Nov. 13, 2018, provisional application No. 62/729,097, filed on Sep. 10, 2018, provisional application No. 62/716,472, filed on Aug. 9, 2018, provisional application No. 62/697,438, filed on Jul. 13, 2018.

(51) Int. Cl.
*B41M 1/04* (2006.01)
*B41J 2/21* (2006.01)

(56) References Cited

U.S. PATENT DOCUMENTS

| | | | |
|---|---|---|---|
| 7,700,263 B2 | 4/2010 | Overend | |
| 9,458,334 B1 | 10/2016 | Samuel | |
| 9,458,339 B2 | 10/2016 | Umberto | |
| 9,550,898 B2 | 1/2017 | Loccufier | |
| 9,701,856 B2 | 7/2017 | Loccufier | |
| 9,714,355 B2 | 7/2017 | Illsley | |
| 9,796,865 B2 | 10/2017 | Claes | |
| 2011/0124768 A1* | 5/2011 | Claes | C09D 11/101 522/182 |
| 2012/0238691 A1* | 9/2012 | Hironaka | C09D 11/101 524/548 |
| 2014/0296420 A1 | 10/2014 | Baptista | |
| 2014/0347429 A1* | 11/2014 | Gould | C09D 11/101 347/100 |
| 2015/0124032 A1* | 5/2015 | De Mondt | B41J 11/002 347/102 |
| 2015/0225585 A1 | 8/2015 | De Rossi | |
| 2015/0361284 A1* | 12/2015 | Herlihy | C09D 11/101 522/18 |
| 2017/0198156 A1* | 7/2017 | Lawrence | C09D 11/101 |
| 2018/0022947 A1 | 1/2018 | Lapin | |

FOREIGN PATENT DOCUMENTS

| | | |
|---|---|---|
| WO | WO2013/093414 A2 | 6/2013 |
| WO | WO2015/148094 | 10/2015 |
| WO | WO2016/158209 | 10/2016 |
| WO | WO2016/207057 | 12/2016 |
| WO | WO2017/144409 | 8/2017 |
| WO | WO2017/151137 | 9/2017 |
| WO | WO2017/157615 | 9/2017 |
| WO | WO2017/180491 | 10/2017 |
| WO | WO2017/180494 | 10/2017 |
| WO | WO2017/180496 | 10/2017 |
| WO | WO 2018/022590 A1 | 2/2018 |

OTHER PUBLICATIONS

Written Opinion of the International Searching Authority issued in International Application No. PCT/GB2019/051856, dated Sep. 2, 2019.
International Preliminary Report on Patentability (Chapter II of the Patent Cooperation Treaty) issued in International Application No. PCT/GB2019/051856, dated Jun. 16, 2020.

* cited by examiner

ELECTRON BEAM CURABLE COMPOSITIONS COMPRISING POLYOLS

CROSS REFERENCE TO RELATED APPLICATIONS

The present application is a § 371 National Phase application based on PCT/GB2019/051856 filed Jul. 1, 2019, which claims the benefit of U.S. Provisional Application Nos. 62/697,438, filed Jul. 13, 2018, 62/716,472 filed Aug. 9, 2018, 62/729,097 filed Sep. 10, 2018, 62/760,142 filed Nov. 13, 2018 and 62/818,772 filed Mar. 15, 2018, the subject matter of each of which is incorporated by reference in their entirety.

The present invention relates to the use of alcohols, and especially polyols, such as diethylene glycol, triethylene glycol, trimethylolpropane and glycerol, to promote the electron beam curing of free radically polymerizable compositions.

Currently, there is renewed interest in the use of electron beam curing, particularly for single pass inkjet printing. It is worthwhile considering the reasons for this renewed interest. As inkjet printhead technology develops there is a drive to faster frequency jetting to deliver both improved print quality and faster press speeds. A consequence of this ongoing printhead development is that the viscosity requirement of the inks is becoming ever lower. Photoinitiators, and especially polymeric and multifunctional types used in the formulation of low migratable compositions can have a significant impact on an ink's viscosity. Furthermore, unless the inks are cured under an inert atmosphere, the impact of oxygen inhibition on lower viscosity inks becomes ever more pronounced and this requires the use of higher concentrations of photoinitiators. A further issue with UV-curable inkjet solutions for low migration applications is that of being able to achieve satisfactory cure through relatively thick ink sections. For example, in complex print designs where composite colours are applied over a backing white ink layer it is possible that the total ink thickness can be in excess of 20 µm. The UV attenuation through the ink film resulting from the pigments and photoinitiators can result in very little incident UV light penetrating through to the base layers of the print. Consequently, it is likely that the cure of the ink at the base levels of the print will be poor with potentially high concentrations of residual uncured monomer. For example, an 8 µm layer of white inkjet ink with 25% $TiO_2$ pigment, overprinted with an 8 µm layer of a yellow inkjet ink (based on pigment yellow 13 at 3.8%), could absorb over 90% of the incident UV light across the UVA, UVB and UVC (down to 225 nm) parts of the UV spectrum, even without taking into account the absorption that would occur from the inclusion of photoinitiators. Clearly, without full UV-cure between printing stations on a UV-inkjet single pass press the capability of achieving satisfactory cure with UV, regardless of the lamp type used is going to be restricted by such UV attenuation factors. EB-cure is much more penetrating than UV-cure and is thus able to more fully cure the thicker ink films deposited by inkjet printing. Indeed, this is an aspect that is incorporated into the current invention.

A particular objective of the present invention is to reduce the amount of contamination from cured inks/coatings in packaging applications. The present invention addresses this problem via the reduction or elimination of migratory compounds which are present in conventional inks/coatings and which cause contamination (i.e. compounds with a low migration limit), and replacing such compounds with compounds which have high migratory limits, while retaining the desired functionality. Surprisingly, the present inventors have found that non-acrylated substances provide a solution to this problem. The present invention covers the most surprising finding that the inclusion of alcohols, and especially polyols (substances comprising 2 or more hydroxyl groups), such as diethylene glycol, triethylene glycol, trimethylolpropane and glycerol can promote the EB-curing of compositions comprising ethylenically unsaturated monomers and oligomers.

Thus, the present invention provides Electron Beam (EB) curable compositions comprising alcohol containing substances, which are essentially free of ethylenically unsaturated groups, according to the following expression:

wherein $R^1$ is any organic residue, where $R^2$ is a hydrogen or any organic residue, and n is any number equal to or greater than one. Thus, the invention provides EB-curable compositions comprising an alcohol of formula $R^1—(CHR^2OH)_n$ which are essentially free of ethylenically unsaturated groups.

The inclusion of such compounds into compositions suitable for inkjet printing which further comprise blends of acrylate monomers has been shown to provide a considerable reduction in the amount of uncured monomer present in an EB-cured ink film. This is an important finding for applications where high conversion of monomers and oligomers (especially of inkjet compositions) during EB cure is beneficial; such as the printing of food packaging, pharmaceutical packaging, personal care packaging, etc. As well as inkjet, this finding will have potential in other printing/coating applications where low migration of monomers and oligomers from EB-cured inks and coatings is required, such as flexographic and gravure printing. The use of and alcohols and especially polyols such as glycerol, trimethylolpropane, propylene glycol and triethylene glycol which are generally recognised as safe and have specific migration limits into food in excess of 6 mg/Kg (in Europe) is advantageous, as significant concentrations of such polyols can be incorporated into a formulation without running the risk of any migration of these polyols from a cured ink or coating into a packaged foodstuff exceeding the migration limit. To put this into context, let's assume that an inkjet composition, comprising 10% (w/w) of triethylene glycol (TEG), is applied at 10 µm, onto 100% of the surface area of the standard European model package (600 $cm^2$ package area per Kg of foodstuff). If all the TEG from the ink migrated into the foodstuff, which is most unlikely, then this would equate to the equivalent of the specific migration limit (SML) for this compound of 60 mg/Kg. Thus, the use of such polyols in EB-curable inks and coatings of the invention is highly beneficial, not just because of their capacity to significantly reduce the amounts of uncured monomers (and oligomers) after EB cure, but also due to their benign nature which results in minimal risk from their own migration. To ensure this, it is a further aspect of the invention that the concentration of any polyol should be less than 25.0% (w/w) of the composition, preferably less than 20.0% (w/w) and more preferably less than 10.0% (w/w) of the composition. In a further aspect of the invention, the total concentration of polyol substances should be less than 25.0% (w/w) of the composition, preferably less than 20.0% (w/w) and more preferably less than 10.0% (w/w) of the composition. The concentration of said polyol is preferably at least 2.0% (w/w), preferably at least 3.0% (w/w), preferably at least 4.0% (w/w), and preferably about 5.0% (w/w) of the composition. The concentration of said polyol is preferably from 4.0% (w/w) to about 10.0% (w/w). Advantageously, the concentration of said polyol is no more than 7.5% (w/w) or no more than 5.0% (w/w) of the composition.

As will become apparent from the review of the prior art, where solvents have been incorporated into energy-curable inkjet compositions in the past they have been done so to reduce the viscosity of the composition and to enable potentially lower film weights after evaporative drying of the solvent. To achieve the full benefit of the incorporation of the alcohols according to the invention it is most desirable that they are not evaporatively removed prior to the EB-curing stage. Thus, those alcohols having relatively high boiling points are preferable, and a further aspect of the invention is that the boiling points of any alcohol used in the current invention should preferably be greater than 150° C., and more preferably greater than 170° C.

As mentioned previously, no records of the use of alcohols, and especially polyols, and especially those which are essentially free of ethylenically unsaturated groups, to promote the EB-cure of free-radically polymerizable compositions have been identified in the prior art. The finding that such compounds can promote EB-curing of inks and coatings is not only surprising but is counter to the perceived wisdom that non-reactive substances like these can have such a profound effect. The inventors do not wish to be bound to any particular theory but consider that alcohols encompassed by the invention promote cure under irradiation by electron beam by generating free radicals that can initiate the polymerisation of ethylenically-unsaturated monomers and oligomers. The most likely mechanism for this postulate is the generation of free radicals at the α-carbon to the alcohol by the scission of a proton to produce the required free radical which initiates the free radical polymerisation of ethylenically unsaturated substances (especially acrylates).

The present application describes a number of examples suitable for inkjet printing, but it should be understood that the invention covers compositions that may be applied by any other coating/printing process where the effect of the inclusion of the alcohol containing substances, and especially of polyols having boiling points greater than 170° C., would be beneficial. Thus, flexographic, offset and gravure printing processes are covered by the current invention, as are roller, spray, and other coating methods.

WO2011/021052 describes UV-curable inkjet compositions comprising greater than 30% (w/w) of solvent. The solvent is removed evaporatively before the inks are UV-cured. The capacity for any hydroxyl-functional material, and especially polyols to enhance the cure under EB is neither described not alluded to.

WO2013/093414 similarly describes solvent containing UV-curable inkjet compositions, with the intention of printing food packaging. Again, the solvent is evaporatively removed prior to UV-curing, and a further requisite to enable this evaporative drying is that the solvents have boiling points of less than 170° C. Again, the capacity of polyols to promote the EB-cure of such compositions is not revealed. It should be noted at this stage that the inks of the current invention use relatively involatile solvents, those with boiling points greater than 170° C., to ensure that they do not evaporate from the ink/coating composition prior to EB-curing so that the desired effect of their use is realised.

WO2017/151137 describes EB-curable inkjet compositions comprising monofunctional monomers bearing a hydroxy group, such as hydroxybutyl acrylate. The capacity of polyol compounds to promote EB-cure is not revealed.

WO2017/180496 and WO2017/180491 describe EB-curable compositions which can optionally comprise ethylenically unsaturated monomers/oligomers comprising poly(alkylene oxide) sub-units. Similarly, WO2015/148094, describes the use of ethylenically unsaturated monomers/oligomers comprising poly(alkylene oxide) sub-units, which promoted the cure of UV-curable compositions. However, none of these records describe the use of polyol containing (poly(alkylene oxide)) substances, which are essentially free of any ethylenically-unsaturated groups, in EB-curable compositions. U.S. Pat. No. 6,846,851 describes the use of poly(ethylene glycol) diacrylates in water-based UV-curable compositions, where they acted as reactive humectants. Again, no mention was made of the use of essentially ethylenically unsaturated free analogous substances for EB-curing.

A number of further sources in the prior art describe the electron-beam curing of inkjet compositions. WO2017/180494 describes how EB cure can be used to improve the resistance properties of inkjet compositions comprising mainly monofunctional monomers. This was likely due to crosslinking occurring under the action of EB radiation. U.S. Pat. No. 7,700,263 describes inkjet compositions comprising blends of acrylate monomers that can be cured under the action of EB. WO2016/158209 describes EB-curable inkjet compositions comprising blends of acrylate monomers and a maleimide-containing oligomer. U.S. Pat. No. 9,458,339 describes EB-curable inkjet compositions, where organic solvent is used to reduce the viscosity. US2018/0022947 describes water-based EB-curable compositions where EB radiation is used to both dry and cure the compositions. None of these records describe, or allude to, the key aspect of the current invention concerning the use of alcohols and more especially polyol substances (substances comprising greater than one hydroxyl group) to promote the EB cure of free radically polymerizable compositions.

As well as inkjet, electron beam radiation of electrographic toner digital printed matter has also been described. WO2017/144409 and WO2017/157615 describe how the thermal resistance of printed matter produced with liquid electrography can be improved via EB cure, no doubt due to the capacity of EB to cause crosslinking in the polymeric component of such prints, as the inks used are essentially free of ethylenically unsaturated groups. A likely disadvantage of such a process is the relatively slow printing speeds achievable with the electrographic printing process, typically less than 25 m/min, for the HP2000 Indigo press used. WO2017/144409 and WO2017/157615 are preceded by U.S. Pat. No. 7,208,257 which similarly described how EB can be used to cure a digital toner print, in this case produced by a dry toner printing method.

A number of patents describe UV-curable low migration inkjet compositions. U.S. Pat. No. 9,714,355 describes compositions comprising blends of low migration photoinitiators, including type I (cleavage) photoinitiators. U.S. Pat. No. 9,550,898 similarly describes UV-curable low migration inkjet compositions which also contain acylphosphine oxide photoinitiators as the type I photoinitiator. U.S. Pat. No. 9,796,865 describes UV-curable low migration inkjet compositions comprising hybrid monomers such as 2-(2-Vinyloxyethoxy)ethyl acrylate ('VEEA'). U.S. Pat. No. 9,701, 856 describes how inkjet compositions comprising essentially VEEA as the only monomer can be combined with thiols to deliver low migration printable solutions.

From the identified prior art, the use of polyol substances, and particularly those essentially free of ethylenically unsaturated groups to promote the cure of free-radically polymerizable compositions under the action of electron beam radiation has not been revealed. The capacity of such substances to significantly reduce the amount of uncured ethylenically unsaturated monomers in electron beam cured coatings and inks is clearly beneficial, especially in sensitive applications where high conversion of monomers is advantageous, such as the printing and coating of food packaging, pharmaceutical packaging, and the like. Increasing the conversion of ethylenically unsaturated monomers during EB-curing will consequently minimise the amount of unbound monomer that could diffuse from the printed ink or coating and cause contamination issues.

What is most surprising is that the polyol compounds used in formulations and processes according to the current invention, which are preferably essentially free of ethylenically unsaturated groups, for example triethylene glycol, glycerol and trimethylolpropane are so effective in reducing the amount of uncured monomer in electron beam cured inks. This is a most unexpected finding and would not likely be anticipated by those skilled in the art. Indeed, it might be expected that the use of such compounds would have a deleterious impact on the EB-cure performance as they would act as diluents.

The use of EB-promoting compounds according to the current invention is especially useful for low migration printing and coating applications, and more especially of food packaging where the lowest possible levels of uncured monomers in printed or coated articles would be desirable. In respect of any possible contamination of packaged foodstuffs arising from the print or coating, the use of compounds such as propylene glycol, glycerol and triethylene glycol is advantageous since they are generally recognised as being safe. Indeed, compounds such as glycerol are often used as humectants in foods intended for human consumption. In the EU, glycerol, propylene glycol and triethylene glycol have migration limits of 60 mg/Kg (60 mg per Kg of foodstuff).

As is apparent from the foregoing, the identified prior art has not disclosed, or alluded to, the use of polyol substances of the current invention, to promote the cure of compositions comprising ethylenically unsaturated monomers and oligomers under the action of EB radiation.

This will be advantageous in printing and coating applications where the maximum conversion of monomers and oligomers is desirable, such as the printing and coating of food packaging. Compared with commercially available EB-inkjet presses the current invention will enable considerably faster press speeds, in excess of a minimum 50 m/min will be possible. This is all achievable due to the most surprising finding that the polyol substances of the current invention dramatically improve the cure response of free radically polymerizable inks and coatings.

Compared with the prior art in the area of UV-curable low migration, the compositions of the current invention, being largely free of photoinitiators (low concentrations of photoinitiators may be incorporated as a further aspect of the invention), and with the capability of curing thick ink and coating films will produce low levels of unbound materials that could potentially migrate and cause contamination issues. This is of particular importance for the printing of food packaging.

Another potential advantage of the invention is that EB radiation is also effective at sterilising articles. Therefore, a further potential benefit of the invention is that it will allow for in-line printing and sterilisation of food packaging in a food packaging filling operation. This would be especially useful for aseptic packaging applications. Although Tetrapak have described the outline of such a digital printing process (WO2016/207057) they were not able to disclose any composition or actual printing process that could deliver such a process.

EB-curing of digital electrographic prints has been described by both Amcor and Xerox. However, compositions and processes of the current invention are advantageous in two ways. Firstly, the press speeds that can be economically reached currently with electrographic printing processes are slow, typically less than 25 m/min. The current invention, based upon the power outputs of commercially available EB-emitters (such as the EBeam Compact unit) will allow for press speeds in excess of at least 50 m/min, more likely in excess of 60 m/min, with the likelihood that speeds in excess of 70 m/min will be achieved, whilst at the same time delivering the desired low levels of migratable monomer from cured prints. For single pass narrow web inkjet printing this is close to the maximum press speeds currently available. More powerful EB-units will allow for even faster press speeds. Secondly, inkjet printing being a non-impact process and not requiring any heating process during the printing operation enables its use on sensitive substrates such as low-density polyethylene and heat-sealable plastic lidding films.

Based on the identified prior art, the use of polyol substances according to the invention (being essentially free of ethylenically unsaturated groups) to promote the cure of compositions comprising ethylenically unsaturated monomers under the action of electron beam irradiation has not been previously described. In particular, the usefulness of the invention with respect to the printing or coating of food packaging articles has not been previously disclosed. Furthermore, the capacity of such substances to promote the EB-cure of compositions comprising ethylenically unsaturated monomers and oligomers more so than materials such as poly(ethylene glycol diacrylate) as revealed in WO2017/180496 is a most surprising finding and one not anticipated by the prior art.

DETAILED DESCRIPTION OF THE INVENTION

Definitions

EB Curing. Compositions prepared according to the present invention are suitable for curing under the action of electron beam (EB) radiation. EB curing describes the use of electron beam radiation to polymerize a combination of monomers and oligomers onto a substrate. In the case of the invention the monomers and oligomers used are those which polymerise free radically, and hence contain ethylenically unsaturated groups, such as acrylate.

Low Migration: The compositions of the current invention lend themselves to applications including the printing of food packaging, pharmaceutical packaging, personal care and household packaging, display boards in supermarkets, etc. In all these applications it is advantageous that the EB-cured ink, or coating, contains minimal amounts of uncured material that could leach ('migrate') out of the ink into the surrounding environment thereby causing unwanted contamination. This is of particular concern for food packaging where any contamination of the packaged food from undesirable, migratable, ink components should be minimized.

UV Pinning. UV pinning is the process of applying a dose of low intensity UV light to a UV curable ink. This results in the ink developing higher viscosity, or gelling, but remaining short of the desired full cure. This process is useful in improving the achievable print quality by limiting drop spread and ink bleed from subsequent printing operations. It is a process suited to inkjet and to a lesser extent flexographic printing.

Molecular Weight. Unless otherwise stated, a reference to "molecular weight" or "average molecular weight" is preferably to the number average molecular weight ($M_n$). The molecular weight can be measured by those techniques known in the art such as gel permeation chromatography. For instance, molecular weight determination may be conducted on a Hewlett-Packard 1050 Series HPLC system equipped with two GPC Ultrastyragel columns, 103 and 104 Å (5 μm mixed, 300 mm×19 mm, Waters Millipore Corporation, Milford, Mass., USA) and THF as mobile phase. Preferably, molecular weight is calculated by comparison with a polystyrene standard. The skilled person will appreciate that this definition of molecular weight applies to polymeric materials which typically have a molecular weight distribution. The molecular weight of non-polymeric compounds, such as the simple molecules of glycerol and trimethylolpropane, are defined and calculated on the basis of the molecular structure of the compound.

The term "essentially free of any ethylenically unsaturated groups", as used herein to describe the alcohol (i.e. hydroxyl) containing substances of utility in the present invention, particularly refers to ethylenically unsaturated groups which are, or comprise, acrylate groups. As noted hereinabove, it is surprising that such non-acrylated substances have such utility. It will be appreciated that such non-acrylated alcohol i.e. hydroxyl) containing substances may optionally comprise other unsaturated groups, for instance aromatic hydrocarbons, as described elsewhere herein.

The present invention describes the most surprising finding that polyol compounds such as glycerol and trimethylolpropane can promote the cure of compositions comprising monomers and oligomers bearing ethylenically unsaturated groups, such as acrylates, under the action of electron beam (EB) radiation. This surprising finding realizes its effect by delivering lower amounts of uncured monomer after EB-curing compared with compositions that do not contain such compounds. This finding, which to the best of the inventors' knowledge, has not been previously described or alluded to in the prior art. The finding has particular relevance for applications such as the printing of food packaging, which require that any ink or coating after application has low levels of substances that might migrate from the ink and/or coating and thence contaminate the surrounding environment, in case of food packaging the foodstuff itself. With the increasing awareness of the potential for contamination risks associated with food packaging, then any printing/coating process that can deliver an acceptably low migration risk has considerable worth. The current invention, via the use of compositions comprising polyols, provides a solution in this respect.

The invention is directed towards coating and ink compositions comprising any blends of ethylenically unsaturated monomers and oligomers, and especially those monomers and oligomers comprising acrylate groups. Compositions according to the invention may be applied by any coating or printing method but flexographic and especially inkjet printing are preferred methods.

The surprising finding of the invention is that alcohols and especially polyols which promote the EB-cure of the compositions do so without having any polymerizable (ethylenically unsaturated) groups incorporated into their structure. This most surprising finding has not been disclosed, or alluded to, in the prior art and is one which runs counter to currently perceived wisdom. The inventors do not wish to be bound by any theory as to why this should be the case but conjecture that polyols, such as glycerol and triethylene glycol, are able to act as initiators of free radical polymerization. They may achieve this under the action of EB radiation by the ready formation of free radicals at the α carbon-hydrogen to the alcohol. This is supported by the examples where the diethyl ether of diethylene glycol showed no observable effect in lowering the amount of uncured monomer during EB-cure, whereas diethylene glycol produced a very pronounced lowering of the amount of uncured monomer.

Regardless of the reason for the enhanced EB-cure response achievable with the substances of the invention, it should be understood that any substance comprising one or more hydroxyl groups according to the following general expression may be used:

$$R^1-(CHR^2OH)_n \qquad (1)$$

Where $R^1$ may be any organic residue, and where $R^2$ may be a hydrogen or any organic residue. In this instance an organic residue refers to any possible sub-unit that may be bound to the polyol of the invention and includes, but is not limited to; alkanes, aromatic hydrocarbons, heterocyclics, polyesters, polyamides, polyacrylics, styrene-acrylic copolymers, polyurethanes, polyethers. In the case of polyethers, the invention encompasses polyols which have been reacted with ethylene oxide, propylene oxide and higher alkylene oxides. Polyethers encompassed by the invention also include poly(ethylene glycol)s, poly(propylene glycol)s and higher poly(alkylene oxide)s. n can be any number equal to or greater than one, preferably equal to or greater than two.

It is further preferred that the polyol used in the invention should have a boiling point of greater than 150° C., preferably greater than 170° C., and most preferably greater than 180° C. at atmospheric pressure (760 mmHg). A further aspect of the invention is that the molecular weight of the polyol used should be less than 2,000 and more preferably less than 1,000, and preferably less than 500

There is no restriction on the amount of polyol used in the inventive compositions. However, it is preferred that greater than 1.0% (w/w) and less than 30.0% (w/w) is used, more preferably between 1.0 and 20.0% (w/w) and even more preferably between 1.0 and 10.0% (w/w).

Although compositions according to the invention are especially suited to flexographic and more particularly inkjet ink compositions, it should be understood that coatings and inks applicable by any other method are covered by the invention. For example, EB-curable offset inks and coatings applied by roller, spray or curtain coating methods.

In a further aspect of the invention, although there is no upper limit of EB dose, compositions of the invention are preferably cured using EB doses of 50 kGy or less, more preferably 40 kGy or less and most preferably with EB doses of 35 kGy or less. Similarly, there is no limit on the accelerating voltage used in generating the EB radiation. However, it is preferable that accelerating voltages of 70 keV or greater are used, preferably 80 keV or greater, and most preferably 100 keV, or greater. Where compositions of the invention are printed or coated on web fed presses, there is no limit on the minimum press speed. However, especially for inkjet printing, it is preferred that the minimum press speed is 40 m/min or greater, more preferably 50 m/min or greater and most preferably 60 m/min or greater. It should be noted that with developing printhead and EB curing unit technology developments that press speeds in excess of 100 m/min could be achievable with compositions prepared according to the current invention.

The invention further encompasses the following relationship between the electron beam dose, the accelerating voltage used and the press speed:

$$X=(A \cdot B/C)<100$$

Where A is the EB dose in kGy, B is the accelerating voltage in keV and C is the press speed in m/min.

In a further aspect to the invention, the inks and coatings may be applied in-line with further packaging converting and (food) filling operations for aseptic packaging.

In yet a further aspect covered by the invention is the use of the electron beam radiation to facilitate other beneficial processes in the production of food packaging, in particular. Thus, the application of electron-beam curable primers, varnishes and adhesives in-line with inks and coatings of the invention are also covered by the current invention in terms of their being applied prior to and after the printing of the inks and coatings described by the invention. In particular, the use of electron beam curing to improve the resistance of gas barrier coatings comprising poly(vinyl alcohol) or ethylene-vinyl alcohol copolymers applied as either a primer layer or as an overprint varnish are covered by the invention. This has the benefit of improving the resistance of such gas barrier coatings to water and steam and also improves their oxygen barrier performance, in particular, at high relative humidities, especially those in excess of 50%. The use of electron-beam curable adhesives in the preparation of multilayer plastic laminates is also covered by the invention. This is an important factor for the flexible packaging market where lamination of several plies of flexible plastic film may be required to deliver the required properties of the food packaging. The use of an electron-beam curable adhesive will allow the rapid generation of stable plastic laminate films; enabling the rapid delivery of finished printed plastic laminate films into the supply chain. This is clearly advantageous for digital printing where rapid turnaround is required, and which would be an issue with the use of conventional adhesives, such as the 2-pack isocyanates, which can take a number of days to fully cure. The use of conventional adhesives, requiring laminates to be stored for a number of days before delivery, would limit the utility of digital printing in this sector as it would remove a key advantage of digital printing, namely the fast turnaround and short delivery times. Indeed, this has already been recognised in the industry by HP who supply a thermal lamination process via their 'Pack-Ready' technology. This thermal lamination process is designed to be used in conjunction with the HP Indigo liquid electrographic printing process to deliver on-demand laminates without recourse to the aforementioned delay required with conventional adhesives used in the flexible packaging industry.

In yet a further aspect of the invention, compositions of the current invention may optionally comprise any blend of photoinitiators. Such compositions may then be cured by a combined UV and EB curing process, as revealed by WO2017/180491 and WO2017/180496. Especially preferred photoinitiators are those that are effective under the output from UV-LED sources. The combined UV and EB curing process of the invention is useful to pin an ink layer prior to subsequent printing of further inks. Where the inks or coatings of the invention are intended for the application to food packaging then those photoinitiators having low migration potential should be used. Suitable photoinitiators will be described subsequently.

Compositions of the invention may comprise any blend of ethylenically unsaturated monomers and oligomers. It will be appreciated that the term "any blend of ethylenic ally unsaturated monomers and oligomers" means that the composition can comprise one or more of such monomers and/or one or more of such oligomers, and preferably comprises at least one ethylenically unsaturated monomer and at least one ethylenically unsaturated oligomer. Where the compositions are intended for the printing or coating of food packaging it is preferred that the concentration of monofunctional monomers be less than 20%, preferably less than 10% and most preferably less than 5% by weight of the total composition.

There is no restriction on the type, blend or concentration of free radical photoinitiators used and can include any of, but not limited to the following (and combinations thereof):

α-hydroxyketones such as; 1-hydroxy-cyclohexyl-phenyl-ketone; 2-hydroxy-2-methyl-1-phenyl-1-propanone; 2-hydroxy-2-methyl-4'-tert-butyl-propiophenone; 2-hydroxy-4'-(2-hydroxyethoxy)-2-methyl-propiophenone; 2-hydroxy-4'-(2-hydroxypropoxy)-2-methyl-propiophenone; oligo 2-hydroxy-2-methyl-1-[4-(1-methyl-vinyl)phenyl]propanone; bis [4-(2-hydroxy-2-methylpropionyl)phenyl]methane; 2-Hydroxy-1-[1-[4-(2-hydroxy-2-methylpropanoyl)phenyl]-1,3,3-trimethylindan-5-yl]-2-methylpropan-1-one and 2-Hydroxy-1-[4-[4-(2-hydroxy-2-methylpropanoyl)phenoxy]phenyl]-2-methylpropan-1-one;

acylphosphine oxides such as; 2,4,6-trimethylbenzoyl-diphenylphosphine oxide; ethyl (2,4,6-trimethylbenzoyl) phenyl phosphinate, bis-(2,4,6-trimethylbenzoyl)-phenylphosphine oxide; and bis(2,6-dimethoxybenzoyl)-2,4,4-trimethylpentylphosphinoxide;

α-aminoketones such as; 2-methyl-1-[4-(methylthio)phenyl]-2-morpholinopropan-1-one; 2-benzyl-2-dimethylamino-1-(4-morpholinophenyl)-butan-1-one; and 2-dimethylamino-2-(4-methyl-benzyl)-1-(4-morpholin-4-yl-phenyl)-butan-1-one;

thioxanthones such as; 2-4-diethylthioxanthone, isopropylthioxanthone, 2-chlorothioxanthone, and 1-chloro-4-propoxythioxanthone;

benzophenones such as; such as benzophenone, 4-phenylbenzophenone, and 4-methylbenzophenone; methyl-2-benzoylbenzoate; 4-benzoyl-4-methyldiphenyl sulphide; 4-hydroxybenzophenone; 2,4,6-trimethyl benzophenone, 4,4-bis(diethylamino)benzophenone; benzophenone-2-carboxy(tetraethoxy)acrylate; 4-hydroxybenzophenone laurate and 1-[-4-[benzoylphenylsulpho]phenyl]-2-methyl-2-(4-methylphenylsulphonyl)propan-1-one;

phenylglyoxylates such as; phenyl glyoxylic acid methyl ester; oxy-phenyl-acetic acid 2-[hydroxyl-ethoxy]-ethyl ester, or oxy-phenyl-acetic acid 2-[2-oxo-2-phenyl-acetoxy-ethoxy]-ethyl ester;

oxime esters such as; 1-phenyl-1,2-propanedione-2-(O-ethoxycarbonyl)oxime; [1-(4-phenylsulfanylbenzoyl)heptylideneamino]benzoate, or [1-[9-ethyl-6-(2-methylbenzoyl)carbazol-3-yl]-ethylideneamino]acetate.

Examples of other suitable photoinitiators include diethoxy acetophenone; benzil; benzil dimethyl ketal; titanocen radical initiators such as titanium-bis(η 5-2,4-cyclopentadien-1-yl)-bis-[2,6-difluoro-3-(1H-pyrrol-1-yl) phenyl]; 9-fluorenone; camphorquinone; 2-ethyl anthraquinone; and the like.

An amine synergist may also be optionally included in the formulation. Suitable examples include, but are not limited to, the following:

Aromatic amines such as; 2-(dimethylamino)ethylbenzoate; N-phenyl glycine; benzoic acid, 4-(dimethylamino)-, 1,1'-[(methylimino)di-2,1-ethanediyl] ester; and simple alkyl esters of 4-(N,N-dimethylamino)benzoic acid, with ethyl, amyl, 2-butoxyethyl and 2-ethylhexyl esters being particularly preferred; other positional isomers of N,N-dimethylamino)benzoic acid esters are also suitable;

Aliphatic amines such as N-methyldiethanolamine, tri-ethanolamine and tri-isopropanolamine;

Also aminoacrylates and amine modified polyether acrylates, including but not limited to; EBECRYL 80, EBECRYL 81, EBECRYL 83, EBECRYL 85, EBECRYL 880, EBECRYL LEO 10551, EBECRYL LEO 10552, EBECRYL LEO 10553, EBECRYL 7100, EBECRYL P115 and EBECRYL P116 available from ALLNEX; CN501, CN550, CN UVA421, CN3705, CN3715, CN3755, CN381 and CN386, all available from Sartomer; GENOMER 5142, GENOMER 5161, GENOMER 5271 and GENOMER 5275 from RAHN; PHOTOMER 4771, PHOTOMER 4967, PHOTOMER 5006, PHOTOMER 4775, PHOTOMER 5662, PHOTOMER 5850, PHOTOMER 5930, and PHOTOMER 4250 all available from IGM, LAROMER LR8996, LAROMER LR8869, LAROMER LR8889, LAROMER LR8997, LAROMER PO 83F, LAROMER PO 84F, LAROMER PO 94F, LAROMER PO 9067, LAROMER PO 9103, LAROMER PO 9106 and LAROMER P077F, all available from BASF; AGISYN 701, AGISYN 702, AGISYN 703, NeoRad P-81 and NeoRad P-85 ex DSM-AGI.

Polymeric photoinitiators and sensitizers are also suitable, including, for example, polymeric aminobenzoates (GENOPOL AB-1 or AB-2 from RAHN, Omnipol ASA from IGM or Speedcure 7040 from Lambson), polymeric benzophenone derivatives (GENOPOL BP-1 or BP-2 from RAHN, Omnipol BP, Omnipol BP2702 or Omnipol 682 from IGM or Speedcure 7005 from Lambson), polymeric thioxanthone derivatives (GENOPOL TX-1 or TX-2 from RAHN, Omnipol TX from IGM or Speedcure 7010 from Lambson), polymeric aminoalkylphenones such as Omnipol 910 from IGM; polymeric benzoyl formate esters such as Omnipol 2712 from IGM; and the polymeric sensitizer Omnipol SZ from IGM.

Since the compositions of the current invention are intended for use in low migration applications printing and coating applications it is preferred that photoinitiators having low migration potential are used. Therefore, polymeric, polymerizable and multifunctional types are preferred.

Compositions according to the invention may comprise any amount of any blend of free radically polymerizable monomers and oligomers.

Examples of suitable monofunctional ethylenically unsaturated monomers include but are not limited to the following (and combinations thereof), where the terms ethoxylated refers to chain extended compounds through the use of ethyleneoxide, propoxylated refers to chain extended compounds through the use of propylene oxide, and alkoxylated refers to chain extended compounds using either or both ethyleneoxide and propylene oxide. Equivalent methacrylate compounds are also capable of being used, although those skilled in the art will appreciate that methacrylate compounds have lower reactivity than their equivalent acrylate counterparts:

isobutyl acrylate; cyclohexyl acrylate; iso-octyl acrylate; n-octyl acrylate; isodecyl acrylate; iso-nonyl acrylate; octyl/decyl acrylate; lauryl acrylate; 2-propyl heptyl acrylate; tridecyl acrylate; hexadecyl acrylate; stearyl acrylate; iso-stearyl acrylate;

behenyl acrylate; tetrahydrofurfuryl acrylate; 4-t.butyl cyclohexyl acrylate; 3,3,5-trimethylcyclohexane acrylate; isobornyl acrylate; dicyclopentyl acrylate; dihydrocyclopentadienyl acrylate; dicyclopentenyloxyethyl acrylate; dicyclopentanyl acrylate; benzyl acrylate; phenoxyethyl acrylate; 2-hydroxy-3-phenoxypropyl acrylate; alkoxylated nonylphenol acrylate; cumyl phenoxyethyl acrylate; cyclic trimethylolpropane formal acrylate; 2(2-ethoxyethoxy) ethyl acrylate; polyethylene glycol monoacrylate; polypropylene glycol monoacrylate; caprolactone acrylate; ethoxylated methoxy polyethylene glycol acrylate; methoxy triethylene glycol acrylate; tripropyleneglycol monomethyl ether acrylate; diethylenglycol butyl ether acrylate; alkoxylated tetrahydrofurfuryl acrylate; ethoxylated ethyl hexyl acrylate; alkoxylated phenol acrylate; ethoxylated phenol acrylate; ethoxylated nonyl phenol acrylate; propoxylated nonyl phenol acylate; polyethylene glycol o-phenyl phenyl ether acrylate; ethoxylated p-cumyl phenol acrylate; ethoxylated nonyl phenol acrylate; alkoxylated lauryl acrylate; ethoxylated tristyrylphenol acrylate; N-(acryloyloxyethyl)hexahydrophthalimide; N-butyl 1,2 (acryloyloxy) ethyl carbamate; acryloyl oxyethyl hydrogen succinate; octoxypolyethylene glycol acrylate; octafluoropentyl acrylate; 2-isocyanato ethyl acrylate; acetoacetoxy ethyl acrylate; 2-methoxyethyl acrylate; dimethyl aminoethyl acrylate; 2-carboxyethyl acrylate; 4-hydroxy butyl acrylate.

Since compositions prepared according to the current invention are preferably intended for low migration printing and coating applications, including the printing and coating of food packaging then the amount of any monofunctional monomer used should be limited so as to reduce the risk associated with the migration of uncured monomer present in a UV-cured ink or coating. Therefore, another aspect of the invention is that the amount of any individual monofunctional monomer should be 20% (w/w) or less, preferably 10% (w/w) or less, and most preferably 5% (w/w) less of the total composition.

Where monomers are used in the preparation of inventive compositions it is preferable that they be multifunctional with respect to their polymerizable groups. Multifunctional monomers, having 2 or more ethylenically unsaturated groups, such as acrylate, have a greater probability of reacting into the UV-cured ink or coating compared with a monofunctional monomer, thereby reducing the risk of potential contamination arising from uncured monomer. Examples of suitable multifunctional ethylenically unsaturated monomers include but are not limited to the following (and combinations thereof), where the terms ethoxylated refers to chain extended compounds through the use of ethyleneoxide, propoxylated refers to chain extended compounds through the use of propylene oxide, and alkoxylated refers to chain extended compounds using either or both ethyleneoxide and propylene oxide. Equivalent methacrylate compounds are also capable of being used, although those skilled in the art will appreciate that methacrylate compounds have lower reactivity than their equivalent acrylate counterparts:

1,3-butylene glycol diacrylate; 1,4-butanediol diacrylate; neopentyl glycol diacrylate; ethoxylated neopentyl glycol diacrylate; propoxylated neopentyl glycol diacrylate; 2-methyl-1,3-propanediyl ethoxy acrylate; 2-methyl-1,3-propanediol diacrylate; ethoxylated 2-methyl-1,3-propanediol diacrylate; 3 methyl 1,5-pentanediol diacrylate; 2-butyl-2-ethyl-1,3-propanediol diacrylate; 1,6-hexanediol diacrylate; alkoxylated hexanediol diacrylate; ethoxylated hexanediol diacrylate; propoxylated hexanediol diacrylate; 1,9-nonanediol diacrylate; 1,10 decanediol diacrylate; ethoxylated hexanediol diacrylate; alkoxylated hexanediol diacrylate; diethyleneglycol diacrylate; triethylene glycol diacrylate; tetraethylene glycol diacrylate; polyethylene glycol diacrylate; propoxylated ethylene glycol diacrylate; dipropylene glycol diacrylate; tripropyleneglycol diacrylate; polypropylene glycol diacrylate; poly (tetramethylene glycol) diacrylate; cyclohexane dimethanol diacrylate; ethoxylated cyclohexane dimethanol diacrylate; alkoxylated cyclohexane dimethanol diacrylate; polybutadiene diacrylate; hydroxypivalyl hydroxypivalate diacrylate; tricyclodecanedimethanol diacrylate; 1,4-butanediylbis [oxy(2-hydroxy-3,1-propanediyl)]diacrylate; ethoxylated bisphenol A diacrylate; propoxylated bisphenol A diacrylate; propoxylated ethoxylated bisphenol A diacrylate; ethoxylated bisphenol F diacrylate; 2-(2-Vinyloxyethoxy)ethyl acrylate; dioxane glycol diacrylate; ethoxylated glycerol triacrylate; glycerol propoxylate triacrylate; pentaerythritol triacrylate; trimethylolpropane triacrylate; caprolactone modified trimethylol propane triacrylate; ethoxylated trimethylolpropane triacrylate; propoxylated trimethylol propane triacrylate; tris (2-hydroxy ethyl) isocyanurate triacrylate; e-caprolactone modified tris (2-hydroxy ethyl) isocyanurate triacrylate; melamine acrylate oligomer; pentaerythritol tetraacrylate; ethoxylated pentaerythritol tetraacrylate; di-trimethylolpropane tetra acrylate; dipentaerythritol pentaaacrylate; dipentaerythritol hexaaacrylate; ethoxylated dipentaerythritol hexaacrylate.

Examples of monomers comprising free-radically polymerizable groups other than acrylate include N-vinyl amides. Examples of N-vinyl amides include but are not limited to N-vinylcaprolactam (NVC), N-vinyl pyrollidone (NVP), diacetone acrylamide, N-vinyl carbazole, N-acryloxyoxy ethylcyclohexanedicarboximide, N-vinyl imidazole, N-vinyl-N-methylacetamide (VIMA) or acryloyl morpholine (ACMO). Vinyl ethers such as 2-(2-vinyloxyethoxy)ethyl (meth)acrylate (VEEA, VEEM), diethylene glycol divinyl ether(DVE2), triethylene glycol divinyl ether (DVE3), ethyl vinyl ether, n-butyl vinyl ether, iso-butyl vinyl ether, tert-butyl vinyl ether, cyclohexyl vinyl ether (CHVE), 2-ethylhexyl vinyl ether (EHVE), dodecyl vinyl ether (DDVE), octadecyl vinyl ether(ODVE), 1-2-butanediol divinyl ether (BDDVE), 1-4, cyclohexanedimethanol divinylether (CHDM-di), hydroxybutyl vinylether (HBVE), 1-4-cyclohexanedimethanolmono vinylether (CHDM-mono), 1,2,4-trivinylcyclohexane (TVCH), vinylphosphonic acid dimethylester (VPA) or vinylphosphonic acid dimethyl ester (VPADME).

As well as, or in place of, free radically-polymerisable monomers any concentration and type of free-radically polymerizable oligomer, including but not restricted to polyurethane acrylates, polyester acrylates, polyether acrylates and epoxy acrylates may be used.

Where the compositions of the invention require colourants, suitable colorants include, but are not limited to organic or inorganic pigments and dyes. The dyes include but are not limited to azo dyes, anthraquinone dyes, xanthene dyes, azine dyes, combinations thereof and the like. Organic pigments may be one pigment or a combination of pigments, such as for instance Pigment Yellow Numbers 12, 13, 14, 17, 74, 83, 114, 126, 127, 150, 155, 174, 180, 188; Pigment Red Numbers 2, 22, 23, 48:1, 48:2, 52, 52:1, 53, 57:1, 112, 122, 166, 170, 184, 202, 266, 269; Pigment Orange Numbers 5, 16, 34, 36, 71; Pigment Blue Numbers 15, 15:3, 15:4; Pigment Violet Numbers 3, 19, 23, 27; and/or Pigment Green Number 7. Inorganic pigments may be one of the following non-limiting pigments: iron oxides, titanium dioxides, chromium oxides, ferric ammonium ferrocyanides, ferric oxide blacks, Pigment Black Number 7 and/or Pigment White Numbers 6 and 7. Other organic and inorganic pigments and dyes can also be employed, as well as combinations that achieve the colors desired.

The EB-curable compositions of the invention may also contain other components which enable them to perform in their intended application. These other ink components include, but are not restricted to; stabilizers, wetting aids, slip agents, inert resins, antifoams, fillers, rheological aids, amine synergists, etc.

The compositions of the invention may also optionally comprise any blend of acrylic polymer or copolymer which is dissolved into it. These polymers are usually prepared by the (thermal) free radical polymerization of blends of monomers including, but not restricted to, styrene, butyl (meth) acrylate, ethyl (meth)acrylate, methyl (meth)acrylate, isobutyl (meth)acrylate. The acrylic polymer preferably has a number average molecular weight of less than 20,000 g/mole and more preferably less than 10,000 g/mole. The molecular weight of such polymers can be measured by those techniques known in the art such as gel permeation chromatography. Examples of acrylic polymers include those supplied from Dianal, Elvacite Rohm and Haas and DSM, amongst others. The acrylic polymer is preferably present in the compositions at a concentration of between 2 and 20% (w/w).

Compositions of the current invention are preferably essentially free of any aprotic solvent, and protic solvents with boiling points of less than 150° C. However, if required, compositions of the current invention can be diluted with such solvents. Both organic and aqueous solvents may be used to dilute the curable compositions of the invention. The preferred maximum amount of any solvent that could be included in an ink composition is 10% (w/w).

The compositions prepared according to the invention are particularly suited to the preparation of inkjet, flexographic and offset printing inks and coatings.

Low migration compositions according to the current invention when (partially) cured (pinned) under the action of UV light prior to the EB-curing process preferably use photoinitiators having low migration potential. Any combination and concentration of low migration potential photoinitiators may be used and types include, but are not restricted to; polymeric, polymerizable, difunctional, multifunctional photoinitiators. Both type I and type II photoinitiators within those classes are suitable. Suitable polymeric photoinitiators have previously been described. Other photoinitiators suitable for low migration applications include, 1-[4-(2-Hydroxyethoxy)-phenyl]-2-hydroxy-2-methyl-1-propane-1-one, Oligo-[2-Hydroxy-2-methyl-1-((4-(1-methylvinyl)phenyl) propanone], Poly(oxy-1,2ethanedyil)-alpha-(4-(dimethylamino)benzoyl)-omega-((4-(dimethylamino) benzoyl)oxy)-(9Cl), 2-Hydroxy-1-{4-[4-(2-hydroxy-2-methyl-propionyl)-benzyl]-phenyl}-2-methyl-propan-1-one, 2-hydroxy-1-[4-(4-(2-hydroxy-2-methylpropionyl) phenoxy)phenyl]-2-methyl propan-1-one. Photoinitiators which are suitable for low migration may include any of those listed in EUPIA's 'Suitability List of Photo-initiators for Low Migration UV Printing Inks and Varnishes', especially those in Group 1A and 1B. Especially preferred photoinitiators are those which are effective in the UVA part of the UV spectrum. Although any UV light source can be used UV-LED sources are preferred and include, but not limited to, those emitting UV light at 355, 365, 377, 385, 395 and 405 nm. Other possible UV light sources include: high-pressure mercury bulb, a medium-pressure mercury bulb, a xenon bulb, a carbon arc lamp, a metal halide bulb, or sunlight, can be used. It should be appreciated by those skilled in the art that any UV light source may be used to cure compositions prepared according to the current invention.

A stabilizer may also be used in the composition to ensure good pot life of the ink, examples of which are nitroxy based stabilizers such as OHTEMPO, TEMPO, and Irgastab UV10. Phenolic stabilizers such as hydroquinone (HQ), methyletherhydroquinone (MEHQ), butylhydroxytoluene (BHT) and 2,6-di-tert-butyl-N,N-dimethylamino-p-cresol. Nitrosophenylhydroxylamine (NPHA) base inhibitors NPHA, amine salts, and metal salts (Al salt, N-PAL) plus the aromatic amine inhibitors diphenylamine(DPA) and phenylenediamine(PPD). Other suitable stabilizers are florstab UV-1, UV-8, Genorad 16 and 18.

Included in the ink formulation can be a suitable deaerator, these prevent the formation of air inclusions and pinholes in the cured coating. These also reduce rectified diffusion which can cause reliability issues in the printhead. The following, non-limiting, products are available from EVONIK: TEGO AMEX 900, 910, 916, 920, 931, 936, 940, 944, 945, 950, 962, 980, 986.

Defoamers can also be included in the formulation, these prevent the formation of foam during manufacture of the ink and also while jetting. These are particularly important with recirculating printheads. Suitable, non-limiting, defoamers include TEGO FOAMEX N, FOAMEX 1488, 1495, 3062, 7447, 800, 8030, 805, 8050, 810, 815N, 822, 825, 830, 831, 835, 840, 842, 843, 845, 855, 860, 883, TEGO FOAMEX K3, TEGO FOAMEX K7/K8 and TEGO TWIN 4000 available from EVONIK. Available from BYK is BYK-066N, 088, 055, 057, 1790, 020, BYK-A 530, 067A, and BYK 354.

Surface Control Additives are often used to control the surface tension of the ink which is required to adjust the wetting on the face plate of the printhead and also to give the desired drop spread on the substrate or and in the case of multi pass inkjet printing wet on dry drop spread. They can also be used to control the level of slip and scratch resistance of the coating. Suitable surface control additives include but are not limited to TEGO FLOW300, 370, 425, TEGO GLIDE 100, 110, 130, 406, 410, 411, 415, 420, 432, 435, 440, 482, A115, B1484, TEGO GLIDE ZG 400, TEGO RAD2010, 2011, 2100, 2200N, 2250, 2300, 2500, 2600, 2650, 2700, TEGO TWIN 4000, 4100, TEGO WET 240, 250, 260, 265, 270, 280, 500, 505, 510 and TEGO WET KL245 all available from EVONIK. Available from BYK are BYK 333,337, BYK UV3500, BYK 378, 347, 361, BYK UV3530, 3570, CERAFLOUR 998, 996, NANOBYK 3601, 3610, 3650 and CERMAT 258. From CYTEC EBECRYL 350, 1360, MODAFLOW 9200, EBECRYL 341. From SARTOMER the aliphatic silicone acrylate CN9800 may be used.

Where ink and coating compositions are applied to the (non-contact) surface of primary or secondary packaging intended for foodstuffs, then any contamination from the package impacting the foodstuff should fall within the guidelines set out by Article 3 of Regulation (EC) No 1935/2004 (supplemented by EC No 10/2011), as recommended by EUPIA, requiring that materials and articles in contact with food;

"shall be manufactured in accordance with good manufacturing practices, so that under normal or foreseeable conditions of use, they do not transfer their constituents to food in quantities which could:
endanger human health; or
bring about an unacceptable change in the composition of the food; or
bring about a deterioration in the organoleptic characteristics thereof"

EUPIA has recommended that Article 3 of this provision be followed when producing printed matter for food packaging and has produced a detailed guideline for the selection of raw materials intended for printing inks for food packaging, along with guidelines on the testing of printed matter to ensure that regulatory requirements are achieved. Where no SML exists for a specific component then the following migration limits apply;

"A target migration limit of no concern for non-evaluated substances of 10 ppb is the ultimate objective, to be consistent with other food contact materials. In particular, a substance is acceptable if its specific migration does not exceed:
10 ppb, in case of insufficient toxicological data
50 ppb if three negative mutagenicity tests requested by EFSA4 Guidelines are available
above 50 ppb, if supported by favorable toxicological data and/or evaluation done in accordance with the EFSA Guidelines"

(Extract from EuPIA Guideline on Printing Inks applied to the non-food contact surface of food packaging materials and articles, September 2009).

EUPIA also provides guidelines on how to measure the potential level of migratables arising from printed matter. For inks and coatings applied to the non-food contact surface of packaging (i.e. the outer surface), whether that be to the primary packaging or secondary packaging (labels and sleeves) then the most likely route for migratable species from the ink contaminating the foodstuff is by what is known as set-off migration. This is where printed matter is stacked or reeled prior to it being filled with food. Thus, the ink comes into contact with what will be the food-contact surface of the package and migratable components of the ink can diffuse into this surface. When the package is then filled with foodstuff, the contaminants from the ink which have diffused into the contact-surface of the package can then leach into the food causing a potential contamination issue.

Thus, any energy-curable fluid which is applied to either the primary or secondary packaging of foodstuff should not result in contamination of that foodstuff at levels exceeding the limits detailed above.

According to a further aspect of the invention, there is provided the use of alcohol containing substances which are essentially free of ethylenically unsaturated groups, according to the following expression:

$$R^1-(CHR^2OH)_n$$

wherein $R^1$ may be any organic residue, where $R^2$ may be a hydrogen or any organic residue, and n is any number equal to or greater than one, to promote the EB-cure of free-radically polymerizable compositions. The foregoing description of the other aspects of the invention, including the preferences thereof, is equally applicable to this aspect of the invention too.

According to a further aspect of the present invention there is provided a process for preparing a printed substrate comprising printing the composition as defined hereinabove onto a substrate and curing, preferably using an EB dose ≤50 kGy and an accelerating voltage ≥70 kev. It will be appreciated that the foregoing description of the other aspects of the invention, including the preferences thereof, is equally applicable to this aspect of the invention too.

According to a further aspect of the present invention there is provided a printed substrate comprising a composition as defined hereinabove and/or which is obtainable by the printing process as defined hereinabove. Thus, it will be appreciated that the printed article in particular comprises a cured coating derived from a curable composition as defined hereinabove. The substrate is preferably a plastic film. The printed article is preferably a food packaging article. It will be appreciated that the foregoing description of the other aspects of the invention, including the preferences thereof, is equally applicable to this aspect of the invention too.

The present invention has been described in detail, including the preferred embodiments thereof. However, it will be appreciated that those skilled in the art, upon consideration of the present disclosure, may make modifications and/or improvements on this invention that fall within the scope and spirit of the invention.

EXAMPLES

The following examples illustrate specific aspects of the present invention and are not intended to limit the scope thereof in any respect and should not be so construed.

Viscosity Measurements

The viscosities of the inks were measured using a Brookfield DV-II+ Pro Viscometer equipped with Spindle no. 18, at 100 rpm.

Curing the Inks for Extraction Testing

The inks were applied to 23 µm Melinex 813 (a polyester film) at 10 µm, unless otherwise stated, and then cured under the specified EB curing conditions. A Comet ebeam EBLab was used to cure the inks; this unit has a maximum beam energy of 200 keV with doses up to 450 kGy in a single pass possible. Nitrogen inertion was applied until the oxygen level was <200 ppm, with the electron accelerating voltage recorded in keV and the dose of electrons in kGy.

Assessing the Level of Extractable Monomer

The levels of unbound, unreacted monomer residues in a print were determined by a 'total extraction' test. This test involved soaking 30 cm$^2$ of the print in 2 ml of methanol, containing 0.005% (w/w) of MEHQ (stabilizer) for 24 hours at room temperature before the methanol solution was analyzed by GC-MS. The GC-MS was calibrated with known solutions of the monomers and the results are reported as the amount of uncured monomer per unit area of print, expressed as µg/dm$^2$.

Inks were prepared according to the compositions below and stirred until homogeneous using a Silverson mixer.

Ink Examples

TABLE 1

Preliminary Investigation into the Impact of Polyols on EB-Cure. EB-Curable Inkjet Compositions.

| | Comp. Example 1 | Comp. Example 2 | Inv. Example 1 | Inv. Example 2 | Inv. Example 3 | Inv. Example 4 | Inv. Example 5 | Inv. Example 6 | Inv. Example 7 | Inv. Example 8 |
|---|---|---|---|---|---|---|---|---|---|---|
| VEEA | 30.0 | 30.0 | 30.0 | 30.0 | 30.0 | 30.0 | 30.0 | 30.0 | 30.0 | 30.0 |
| 3-MePDDA | 25.0 | 25.0 | 25.0 | 25.0 | 25.0 | 25.0 | 25.0 | 25.0 | 25.0 | 25.0 |
| DPGDA | 4.0 | 4.0 | 4.0 | 4.0 | 4.0 | 4.0 | 4.0 | — | 4.0 | 4.0 |
| Acrylated Amine | 5.0 | 5.0 | 5.0 | 5.0 | 5.0 | 5.0 | 5.0 | 5.0 | 5.0 | 5.0 |
| TMPEOTA | 25.0 | 20.0 | 20.0 | 20.0 | 20.0 | 20.0 | 20.0 | 19.0 | 20.0 | 20.0 |
| PEG400DA | — | 5.0 | — | — | — | — | — | — | — | — |
| Glycerol | — | — | 5.0 | — | — | — | — | — | — | — |
| Trimethylol propane | — | — | — | 5.0 | — | — | — | — | — | — |
| TMP(EO)3 | — | — | — | — | 5.0 | — | — | — | — | — |
| TMP(EO)7 | — | — | — | — | — | 5.0 | — | — | — | — |
| TMP(EO)20 | — | — | — | — | — | — | 5.0 | 10.0 | — | — |
| Penta(EO)5 | — | — | — | — | — | — | — | — | 5.0 | — |
| Penta(EO)15 | — | — | — | — | — | — | — | — | — | 5.0 |
| TegoRad 2200 | 2.0 | 2.0 | 2.0 | 2.0 | 2.0 | 2.0 | 2.0 | 2.0 | 2.0 | 2.0 |
| Cyan Dispersion | 9.0 | 9.0 | 9.0 | 9.0 | 9.0 | 9.0 | 9.0 | 9.0 | 9.0 | 9.0 |
| Total | 100.0 | 100.0 | 100.0 | 100.0 | 100.0 | 100.0 | 100.0 | 100.0 | 100.0 | 100.0 |
| Extractable DPGDA (µg/dm$^2$) | 36.0 | 11.3 | 5.8 | 1.5 | <0.5 | 0.5 | 0.9 | 0.6 | 0.9 | 0.6 |
| Extractable 3-MePDDA (µg/dm$^2$) | 47.0 | 16.8 | 9.0 | 1.8 | <0.5 | 0.7 | 1.3 | 0.8 | 0.8 | 0.7 |
| Extractable VEEA (µg/dm$^2$) | 42.5 | 14.3 | 8.3 | 2.0 | 0.5 | 0.9 | 1.7 | 1.6 | 1.0 | 1.1 |

Notes:

VEEA = 2-(2-vinyloxyethoxy)ethyl acrylate; 3-MePDDA = 3-Methylpentanediol diacrylate; DPGDA = Dipropylene glycol diacrylate; PEG400DA = Poly(ethylene glycol 400) diacrylate; TMPEOTA = Trimethylolpropane ethoxylate triacrylate (3 moles ethoxylation) (Sartomer SR454); Acrylated Amine = Photomer 4771; TMP(EO) 3, 7, 20 = Ethoxylated trimethylol propane with 3, 7 and 20 moles ethoxylation; Penta(EO) 5, 15 = Ethoxylated pentaerythritol with either 5 or 15 moles ethoxylation; Tego Rad 2200 = silicone polyether acrylate, ex. Evonik; Cyan Dispersion = a proprietary dispersion containing 25.0% (w/w) of Pigment 15:4, the remainder comprising the dispersant, stabilizers and DPGDA.

The inks were applied to the PET film at a film weight of 10 μm using a calibrated K-Bar (ex. RK Print) and subsequently cured with an accelerating voltage of 100 keV and a dose of 35 kGy.

It is clear from Table 1 that all the polyols used produced a significant reduction in the amount of uncured monomer in the inks after exposure to the EB radiation. The most effective polyol in this series was trimethylolpropane having 3 moles of ethoxylation (Inventive Example 3). This is a very surprising finding since Inventive Example 3 can be considered as the equivalent of Comparative Example 1 where 5.0% of the trimethylolpropane ethoxylate triacrylate has been replaced with the non-acrylated polyol equivalent. This finding is one not anticipated by the identified prior art. The superior performance of TMP(EO)3 compared with TMP (trimethylolpropane) may be due to its better solubility but may also be due to the presence of the ethylene oxide substitution also contributing to the EB cure. It is likely that poly(alkylene oxide) groups may also contribute to the EB-curing process as they may also act as a center for the generation of free radicals that could promote free radical polymerization. Therefore, as a further aspect of this invention, alcohols and polyols comprising poly(alkylene oxide) sub-units are also encompassed. Thus, those alcohols containing as part of their structures an ether, poly(ethylene glycol), poly(propylene glycol) or higher poly(alkylene oxide) are also covered.

What is also evident from Table 1 is that the polyols used induce a greater lowering of the uncured monomer levels than a poly(ethylene glycol) diacrylate, as revealed in WO2017/180491, WO2017/180496 and WO2015/148094.

The results revealed in Table 1 are most surprising, as they demonstrate that polyol substances, being essentially free of any ethylenically unsaturated groups can have a very pronounced and significant effect upon the lowering of the amount of uncured monomer from an EB-cured coating composition. Clearly, this has particular relevance where such compositions are intended for the use in sensitive printing or coating applications such as the printing of food packaging.

A further series of pigmented compositions, suitable for inkjet printing, were prepared and tested to exemplify the findings revealed through Inventive Examples 1 to 8. For this series of ink examples, the following general formulation was used.

TABLE 2

Formulation details for the Second Set of EB-Curable Inkjet Compositions

| Component | % (w/w) |
| --- | --- |
| VEEA | 30.0 |
| 3-MePDDA | 30.0 |
| TMPEOTA | 11.0-16.0 |
| Polyol | 0, 5.0 |
| Acrylated Amine | 5.0 |
| TG410 | 2.0 |
| Magenta Dispersion | 17.0 |

Notes to Table 2:
TG410 = Tegoglide 410, a polyether silicone surfactant, ex. Evonik;
Magenta Dispersion = a proprietary dispersion containing 21.0% (w/w) of Pigment Red 122, the remainder comprising the dispersant, stabilizers and DPGDA Table 3 provides the details of the polyols used in this second series of experiments, along with the viscosity of the inks at 45° C. The boiling points of the polyols are also provided, by way of reference.

The inks were tested in the same manner as previously, but the EB-curing conditions were 100 keV accelerating voltage and a dose of 25 kGy.

TABLE 3

Magenta Inkjet Compositions comprising Polyols and Polyethers.

| Example | Polyol | Polyol Boiling Point (° C.) | Ink Viscosity (mPa · s) | Extractable DPGDA (μg/dm$^2$) | Extractable 3-MePDDA (μg/dm$^2$) | Extractable VEEA (μg/dm$^2$) |
| --- | --- | --- | --- | --- | --- | --- |
| Comparative 3 | — | — | 8.13 | 148 | 165 | 265 |
| Comparative 4 | PPG750DA | — | 8.21 | 125 | 129 | 192 |
| Inventive 9 | EG | 197 | 9.00 | 112 | 118 | 179 |
| Inventive 10 | DEG | 245 | 7.62 | 38 | 37 | 50 |
| Inventive 11 | TEG | 285 | 8.07 | 31 | 31 | 46 |
| Inventive 12 | Tet.EG | 327 | 7.94 | 44 | 43 | 65 |
| Inventive 13 | PEG200 | >250 | 7.86 | 43 | 44 | 68 |
| Inventive 14 | DEGMEE | 194 | 7.02 | 40 | 46 | 87 |
| Comparative 5 | DEGDEE | 188 | 6.75 | 139 | 166 | 320 |
| Inventive 15 | PG | 188 | 7.35 | 51 | 52 | 85 |
| Inventive 16 | 3-MePD | 249 | 7.65 | 37 | 38 | 60 |
| Comparative 6 | 1-Octanol | 195 | 7.20 | 143 | 161 | 283 |
| Inventive 17 | TMP(EO)3 | >250 | 8.28 | 36 | 36 | 58 |

Notes to Table 3:
PPG750DA = polypropylene glycol) 750 diacrylate; EG = ethylene glycol; DEG = diethylene glycol; TEG = triethylene glycol; Tet.EG = tetraethylene glycol; PEG200 = poly(ethylene glycol) 200; DEGMEE = diethylene glycol monoethyl ether; DEGDEE = diethylene glycol diethyl ether; PG = propylene glycol; 3-MePD = 3-methylpentanediol.

A number of observations can be made from the results provided in Table 3. Firstly, those polyols comprising two or more hydroxyl groups produce a significant lowering of the amount of uncured monomer in the EB-cured ink films. Again, the impact of replacing TMPEOTA with TMP(EO)3 (Comparative Example 3 and Inventive Example 17) on significantly reducing the amount of uncured monomer is seen. Secondly, the simple alcohol 1-octanol produces no significant observable effect in the amount of uncured monomer, whereas the aliphatic diol 3-methylpentanediol does. Thirdly, with the poly(ethylene glycol) series of inks (Inventive examples 9 to 13), a preferred substance is triethylene glycol. The benefit of the presence of the alcohol group can be seen by comparing Inventive examples 10 and 14 and Comparative Example 5 (DEG, DEGMEE and DEGDEE). Etherification of one of the hydroxyl groups of DEG results in a slight increase in the amount of uncured monomer whereas with DEGDEE, where both alcohols have been removed via etherification, the amount of uncured monomer is comparable to Comparative example 3 comprising no alcohol or polyol. These findings indicate a proviso for the use of substances comprising only one alcohol as part of their chemical structure; that is they should further comprise a poly(alkylene oxide) sub-unit. Much like in the first set of experiments the results with 3-methylpentanediol and propylene glycol indicate that simple polyols can induce a significant lowering of the amount of uncured monomer in EB-cured inks and coatings.

What is claimed is:

1. Electron Beam (EB) curable compositions comprising alcohol containing substances, which are essentially free of ethylenically unsaturated groups,
    wherein the alcohol is selected from the group consisting of propylene glycol, trimethylolpropane, glycerol, diethylene glycol, triethylene glycol, tetraethylene glycol, dipropylene glycol, tripropylene glycol, poly(ethylene glycol), poly(propylene glycol), ethoxylated trimethylolpropane, propoxylated trimethylolpropane, ethoxylated pentaerythritol, propoxylated pentaerythritol, ethoxylated ditrimethylolpropane, propoxylated ditrimethylolpropane, ethoxylated dipentaerythritol, propoxylated dipentaerythritol, and combinations thereof,
    wherein the compositions further comprise one or more ethylenically unsaturated monomers, wherein the concentration of monofunctional monomer is less than 20% by weight of the total composition, and
    wherein the compositions are essentially free of any aprotic solvent, and protic solvents with boiling points of less than 170° C.

2. The composition of claim 1, wherein the alcohol is present in an amount from 2-20 wt % and has a molecular weight of less than 2,000.

3. The composition of claim 1, wherein the alcohol has a molecular weight of less than 1,000.

4. The composition of claim 1, wherein the alcohol is selected from the group consisting of propylene glycol, trimethylolpropane, glycerol, diethylene glycol, triethylene glycol, tetraethylene glycol, dipropylene glycol, tripropylene glycol, poly(ethylene glycol), poly(propylene glycol), and combinations thereof.

5. The composition of claim 1, wherein the composition is free of photoinitiators.

6. The composition of claim 1, further comprising any blend of photoinitiators, wherein the total concentration of photoinitiators is less than 5.0 wt %.

7. The composition of claim 1 which is a pigmented inkjet ink, or a pigmented flexo ink, or a pigmented offset ink.

8. A printed substrate comprising the composition of claim 1.

9. The substrate of claim 8 which is a plastic film.

10. A process for preparing an article with a low migration coating or an ink printed thereon comprising;
    applying any number of ink and/or coating compositions according to claim 1 to a substrate and curing the composition preferably using an EB dose ≤50kGy and an accelerating voltage ≥70kev.

11. The process of claim 10, satisfying the following expression:

$$X = A \cdot B / C < 100$$

where A is the electron beam dose in kGy, B is the accelerating voltage in keV and C is the press speed in m/min.

12. An in-line printing and sterilization method for producing aseptic food packaging prior to the filling with foodstuffs, comprising the process of claim 10.

13. The compositions of claim 1, wherein the compositions further comprise one or more pigment dispersions, wherein the one or more ethylenically unsaturated monomers and one or more pigment dispersions, together, are present in the composition at a concentration of 88-93% by weight, based on the total weight of the composition.

14. The composition of claim 13 wherein the maximum amount of any solvent is 10% by weight, based on the total weight of the composition.

15. The composition of claim 14 wherein the alcohol containing substances are present in an amount of from 5-10% by weight, based on the total weight of the composition.

16. The use of alcohol containing substances which are essentially free of ethylenically unsaturated groups, to promote the EB-cure of free-radically polymerizable compositions, wherein the alcohol is selected from the group consisting of propylene glycol, trimethylolpropane, glycerol, diethylene glycol, triethylene glycol, tetraethylene glycol, dipropylene glycol, tripropylene glycol, poly(ethylene glycol), poly(propylene glycol), ethoxylated trimethylolpropane, propoxylated trimethylolpropane, ethoxylated pentaerythritol, propoxylated pentaerythritol, ethoxylated ditrimethylolpropane, propoxylated ditrimethylolpropane, ethoxylated dipentaerythritol, propoxylated dipentaerythritol, and combinations thereof,
    wherein the compositions further comprise one or more ethylenically unsaturated monomers,
    wherein the concentration of monofunctional monomer is less than 20% by weight of the total composition, and
    wherein the compositions are essentially free of any aprotic solvent, and protic solvents with boiling points of less than 170° C.

17. The use of claim 16, wherein the alcohol has a boiling point greater than 150° C.

18. The use of claim 16, wherein the alcohol is used in an amount from 2-20 wt % and has a molecular weight of less than 2,000.

19. The use of claim 16, wherein the alcohol is selected from the group consisting of propylene glycol, trimethylolpropane, glycerol, diethylene glycol, triethylene glycol, tetraethylene glycol, dipropylene glycol, tripropylene glycol, poly(ethylene glycol), poly(propylene glycol), and combinations thereof.

* * * * *